United States Patent [19]

May

[11] Patent Number: 4,725,432

[45] Date of Patent: Feb. 16, 1988

[54] ANTIPERSPIRANT AND DEODORANT STICK COMPOSITION

[75] Inventor: William G. May, Cincinnati, Ohio

[73] Assignee: The Procter & Gamble Company, Cincinnati, Ohio

[21] Appl. No.: 602,848

[22] Filed: Apr. 23, 1984

Related U.S. Application Data

[63] Continuation of Ser. No. 460,973, Jan. 26, 1983, abandoned.

[51] Int. Cl.$^3$ .................. A61K 7/32; A61K 7/34; A61K 7/38
[52] U.S. Cl. .................. 424/66; 424/DIG. 5; 424/65; 424/68; 514/358; 514/643; 514/717
[58] Field of Search .................. 424/65, 66, DIG. 5

[56] References Cited

U.S. PATENT DOCUMENTS

| | | | |
|---|---|---|---|
| 4,126,679 | 11/1978 | Davy | 424/66 |
| 4,151,272 | 4/1979 | Geary | 424/357 |
| 4,229,432 | 10/1980 | Geria | 424/68 |
| 4,265,878 | 5/1981 | Keil | 424/68 |
| 4,280,994 | 7/1981 | Turney | 424/68 |
| 4,331,609 | 5/1982 | Orr | 424/66 |

FOREIGN PATENT DOCUMENTS 1365140  6/1974  United Kingdom .................. 424/68

Primary Examiner—Dale R. Ore
Attorney, Agent, or Firm—Jack D. Schaeffer; Douglas C. Mohl; David L. Suter

[57] ABSTRACT

Solid stick compositions comprising a long-chain fatty alcohol having from about 8 to about 18 carbon atoms in the chain, volatile silicone and $C_{20}$ or longer chain alcohols at levels of from about 1% to about 3% of the total long-chain fatty alcohol present in the compositions. These solid sticks have improved strength and hardness without undue brittleness.

8 Claims, No Drawings

ANTIPERSPIRANT AND DEODORANT STICK COMPOSITION

This is a continuation of application Ser. No. 460,973, filed on Jan. 26, 1983, now abandoned.

BACKGROUND OF THE INVENTION

The present invention relates to solid stick compositions, particularly solid antiperspirant sticks, having satisfactory strength and hardness while exhibiting aesthetically-pleasing attributes.

Many solid stick compositions are available in the art. Typically, these solid sticks are available in two basic forms. One such form is composed of soap/alcohol gel sticks, which may have stability problems. For instance, the combination of soap/alcohol gels with conventional astringent antiperspirant salts, such as aluminum chlorohydrate, can result in unstable gel structures rendering such sticks less aesthetically-pleasing to consumers.

In order to alleviate some of these problems, waxy materials, some in combination with volatile fluids, have been used in the development of solid stick compositions. U.S. Pat. No. 4,126,679, Nov. 21, 1978 to Davy and Drolet; U.S. Pat. No. 4,229,432, Oct. 21, 1980 to Geria; U.S. Pat. No. 4,265,878, May 5, 1981 to Keil; U.S. Pat No. 4,280,994, July 28, 1981 to Turney disclose such compositions. The most commonly used waxy material in sticks of this type long-chain fatty alcohols. Some use such alcohols in combination with volatile silicones. Although these fatty alcohol/volatile silicone solid sticks avoid some of the soap gel problems, they may vary unacceptably in structural hardness and strength. Therefore, formulations are sought which provide strong fatty alcohol-volatile silicone-based sticks without causing those sticks to become too brittle and cosmetically unacceptable.

Surprisingly, the addition of fatty alcohols, $C_{20}$ and longer, produces such a product. That is, not only is the strength of such a stick increased, but that strength enhancement does not result in overly hard, brittle product.

It is an object, of the present invention to provide solid stick compositions containing long-chain higher fatty alcohols and a volatile silicone wherein such compositions contain sufficient $C_{20}$ alcohol and longer chain alcohols to result in a stable and strong final product.

It is a further object of the present invention to not only provide strong final products but to provide aesthetically-pleasing products as well.

Another object of this invention is to provide solid stick compositions as described above which additionally contain astringent antiperspirant salt materials.

These and other objectives will become more apparent from the following disclosure. All percentages and ratios herein are by weight unless otherwise designated.

SUMMARY OF THE INVENTION

The solid stick compositions of the present invention are comprised of from about 5% to about 20% of a long-chain fatty alcohol and from about 35% to about 55% volatile silicone, wherein said compositions also contain an alcohol selected from the group consisting of $C_{20}$ alcohol, alcohols whose chains are longer than $C_{20}$ and mixtures thereof at levels of from about 1% to about 3% of the total long chain fatty alcohols present in said compositions.

DETAILED DESCRIPTION OF THE INVENTION

The present solid stick compositions contain certain essential and may in addition contain other nonessential, optional components. Each component is discussed in detail below.

LONG-CHAIN HIGHER FATTY ALCOHOL

The higher fatty alcohols of the present invention are those having melting points of from about 100° F. to about 150° F. These include fatty alcohols containing from about 8 to about 18 carbon atoms in their chain, preferably from about 12 to about 18 carbon atoms. Examples suitable for use in the invention at hand include cetyl alcohol, stearyl alcohol, myristyl alcohol, lauryl alcohol, and mixtures thereof.

From about 5% to about 20% higher fatty alcohol is present in the solid stick compositions, preferably from about 10% to about 15%.

As indicated above, the compositions described herein also contain from about 1% to about 3%, based on the total weight of the long chain fatty alcohols present (the $C_{12}$–$C_{18}$ alcohols as well as the longer chain alcohols), of alcohols having chain lengths of $C_{20}$ or longer. A preferred alcohol of this type is commercially available $C_{20}$ alcohol which is a mixture of higher fatty alcohols wherein about 50% is $C_{20}$, about 30% is $C_{22}$, with the remainder primarily composed of alcohol chains longer than $C_{22}$. The alcohols useful in the present invention may go up to $C_{26}$ but it is preferred to have the majority in the $C_{20}$–$C_{22}$ range. The level of $C_{20}$ and longer chain alcohols found in the commercially available shorter long-chain fatty alcohols (e.g. stearyl alcohol) generally does not exceed about 0.8%. Only by increasing the level of these alcohols to from about 1% to about 3%, preferably from about 1% to 2%, of the total higher fatty alcohol content will a stronger product result.

VOLATILE SILICONE

The volatile silicones useful in the solid stick compositions of the present invention may be either cyclic or linear with the polydimethylsiloxanes containing from about 3 to about 9, preferably from about 4 to about 5, silicon atoms, being preferred.

The following formula illustrates the cycle volatile polydimethylsiloxanes useful in the solid stick compositions disclosed herein:

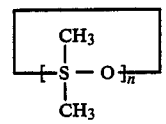

wherein n=3 to 7.

The linear polydimethylsiloxanes contain from about 3 to about 9 silicon atoms per molecule and have the following general formula:

wherein n=1 to 7.

Examples of silicones of the above type include those offered by Dow Corning Corporation, Dow Corning 344, 345 and 200 fluids, Union Carbide, Silicone 7207 and Silicone 7158, and Stauffer Chemical, SWS-03314.

The linear volatile materials generally have viscosities of less than about 5 centistokes at 25° C. while the cyclic materials have viscosities less than about 10 centistokes. "Volatile" means that the material has a measurable vapor pressure. A description of volatile silicones is found in Todd and Byers, "Volatile Silicone Fluids for Cosmetics", *Cosmetics and Toiletries*, Vol. 91, January, 1976, pp. 27–32, incorporated herein by reference.

The amount of volatile silicone used in the present compositions is from about 35 to about 55, preferably from about 40 to about 50%.

OPTIONAL COMPONENTS

The solid stick compositions of the present invention may contain a variety of optional, nonessential components. These components serve a variety of functions such as improving the stability, cosmetics and/or aesthetics of the present compositions.

WAX

A preferred optional component includes a wax such as castor wax, fatty acids, silicone waxes and glycerol monostearate, and mixtures thereof at levels of from about 1% to about 10%, preferably from about 3% to about 10%. If present, the wax is believed to enhance structural stability at higher temperatures.

EMOLLIENT

The emollient component of the present invention is useful in providing an aesthetically-pleasing product. One type of emollient suitable for use in the present solid stick compositions is an ethylene oxide and/or propylene oxide condensation product having the following formula:

$$RO(C_2H_4O)_a(C_3H_6O)_bH$$

wherein R is either hydrogen or a hydrocarbon chain having from about 2 to 20 carbon atoms, preferably from about 4 to about 18, a and b are each from about 0 to about 35, and a+b is from about 5 to about 35.

Examples of such emollients include Fluid AP® (a condensate of about 14 moles of propylene oxide with about 1 mole of butyl alcohol sold by Union Carbide); a polypropylene glycol having molecular weight of about 1200; a polyethylene glycol having molecular weight of about 420; a condensate of 20 moles ethylene oxide and 5 moles propylene oxide with one mole of cetyl alcohol, and mixtures thereof.

Other emollients suitable for use in the present solid stick compositions include fatty acid and fatty alcohol esters and water insoluble ethers such as those disclosed in U.S. Pat. No. 4,202,879, May 13, 1980 to Shelton, incorporated herein by reference and mixtures thereof.

If present, the emollient is used at levels of from about 2% to about 10%, preferably from about 3% to about 7%.

ASTRINGENT ANTIPERSPIRANT

Any aluminum astringent antiperspirant salt or aluminum and/or zirconium complex can be employed herein when the present sticks are intended for use as an antiperspirant. Useful are such salts as aluminum halides, aluminum hydroxyhalides, zirconyl oxyhalides, zirconyl hydroxyhalides, and mixtures thereof. The aluminum salts of this type include aluminum chloride and aluminum hydroxyhalide having the following formula:

$$Al_2(OH)_aCl_b \cdot X\ H_2O$$

a is from about 2 to about 5; a+b=6 and a and b need not be integers; and x is from about 1 to about 6. The manner of preparing such salts is disclosed in U.S. Pat. No. 3,887,692, June 3, 1975 to Gilman, incorporated herein by reference.

Zirconium salts are also useful in the present invention. Such salts include zirconium oxychloride, zirconium hydroxychloride, and zirconium salts of the formula, $ZrO(OH)_{2-a}Cl_a \cdot nH_2O$, wherein a is from about 1.5 to about 1.87 and n is from about 1 to about 7. These types of zirconium salts are discussed in Belgium Pat. No. 825,146, Aug. 4, 1975 to The Procter & Gamble Company, incorporated herein by reference.

Complexes of the previously-discussed astringent salts are disclosed in U.S. Pat. No. 3,679,068, Feb. 12, 1974 to Luedders, et al., incorporated herein by reference. The Leudders et al. patent discloses complexes of aluminum, zirconium and glycine commonly known as ZAG complexes.

The preferred aluminum salt for use in such ZAG complexes is aluminum chlorhydroxide with the preferred zirconium compounds being zirconyl hydroxychloride and other zirconyl hydroxyhalides of the following formula:

$$ZrO(OH)_{2-a}Cl_a \cdot nH_2O$$

wherein a is from about 1.5 to about 1.87 and n is from about 1 to about 7 U.S. Pat. No. 4,120,948, Oct. 17, 1978 to Shelton discusses these preferred ZAG compounds and is incorporated herein by reference.

Other antiperspirant complexes are also suitable for use in the present compositions. For example, U.S. Pat. No. 3,903,258, Sept. 2, 1975 to Siegel, discloses a zirconyl chloride/aluminum hydroxide and aluminum chlorhydroxide complex. U.S. Pat. No. 3,979,510, Sept. 6, 1976 to Rubino discloses complexes composed of particular aluminum, zirconium and aluminum buffer compounds. Additionally, U.S. Pat. No. 3,981,986, Sept. 21, 1976 to Rubino, discloses the aluminum and zirconium complexes with an organic buffer, and U.S. Pat. No. 3,970,748, July 20, 1976 to Mecca, discloses an aluminum chlorhydroxy glycinate complex. All of these patents are incorporated herein by reference.

The levels of these antiperspirant materials range from about 10% to about 70%, preferably from about 15% to about 50%, most preferably from about 15% to about 25% on a pure antiperspirant salt basis. In the case of ZAG type materials glycine is excluded when antiperspirant salt level is determined.

OTHERS

Another optional component of the present invention is inert filler material. This filler material enhances the aesthetic characteristics of the present solid sticks and may serve to stabilize the structure of such sticks.

Among the filler materials suitable for use in the present invention are talc, colloidal silica such as CAB-O-Sil(Cabot. Corp.), clays such as bentonite, and mixtures thereof. The inert filler material comprises from about 0.5% to about 10% of the present solid stick compositions.

Conventional deodorant materials also may be included in the present invention. Suitable deodorants include bacteriostatic quaternary ammonium compounds such as cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, stearyl, trimethyl ammonium chloride and mixtures thereof. Another suitable deodorant material is 2,4,4′trichloro-2′-hydroxydiphenyl ether. If present, these deodorants comprise from about 0.1% to about 1.0% of the composition.

Other optional components include perfumes, pigments, dyes, coloring agents, and the like, at levels individually of from about 0.1% to about 2.0%.

METHOD OF MANUFACTURE

The solid stick compositions of the present invention are made in accordance with well-established methods known to those knowledgeable in the art.

INDUSTRIAL APPLICATION

The present solid stick compositions are useful as vehicles for a wide variety of cosmetic materials. For instance, a preferred use of these solid stick compositions is as antiperspirant sticks. However, these sticks can be used as deodorant sticks as well as other cosmetic vehicles.

The following example is presented as an illustration of the present invention and is not limitative thereof.

EXAMPLE I

An antiperspirant stick was made utilizing the following components:

| Component | Weight % |
| --- | --- |
| Cyclomethicone | 43.95 |
| Fluid AP | 4.99 |
| Stearyl Alcohol | 11.49 |
| Castor Wax | 4.99 |
| Talc | 6.99 |
| Zirconium/Aluminum/Glycine complex | 26.67 |
| Fragrance Masking Agent | 0.80 |
| $C_{20}OH$* | 0.12 |

*This is the commercial $C_{20}$ alcohol mixture described previously.

EXAMPLE II

An antiperspirant stick similar to that described in Example I was prepared but the $C_{20}$ and longer chain alcohol level was only 0.034%. This stick therefore did not have the required amount of such long chain alcohols.

EXAMPLE II

The sticks of Examples I and II were compared for softness and break strength. The softness measurements were made using a penetrometer while the break strength measurements were made using a Chatillon break strength tester. The results of these tests are shown below.

| | Penetration (Tenths of a mm)* | Break Strength (Pounds Force)** |
| --- | --- | --- |
| Example I Product | 78.1 | 11.3 |
| Example II Product | 96.1 | 7.1 |

*The penetration values are determined by using ASTM Method D-5. The measurements are made at least 10 mm from the edge of a stick.
**The breakstrength is determined using a Hunter Force Gauge, Model L-10, 0–30 lb. range. The gauge is attached to a slide which allows the gauge to contact the test stick through a breaker bar at a speed of three inches per minute. The value recorded is the force gauge reading when the stick breaks.

It is seen that the product of the present invention has a greater break strength while also having a lower penetration value.

What is claimed is:

1. An improved solid antiperspirant stick composition comprising
    a. from about 5% to about 20% of a long-chain fatty alcohol having from about 8 to about 18 carbon atoms in its chain;
    b. from about 35% to about 55% volatile silicone; and
    c. from about 10% to about 70% of an astringent antiperspirant salt; wherein the improvement comprises improving the strength of said stick without undue brittleness by additionally including an alcohol selected from the group consisting of $C_{20}$ alcohol, alcohols whose chains are longer than $C_{20}$ and mixtures thereof, at a level of from about 1% to about 3% of the total fatty alcohol level.
2. A solid stick composition as described in claim 1 which additionally contains from about 1% to about 10% of a wax selected from the group consisting of castor wax, fatty acids, silicone waxes, glycerol monostearate, and mixtures thereof.
3. A solid stick composition as described in claim 2 wherein said long-chain fatty alcohol is present at a level of from about 10% to about 15% and is selected from the group consisting of cetyle alcohol, stearyl alcohol, myristyl alcohol, lauryl alcohol, and mixtures thereof.
4. A solid stick composition as described in claim 3 wherein said volatile silicone is selected from the group consisting of cyclic and linear polydimethylsiloxanes having from about 3 to about 9 silicone atoms in their chain.
5. A solid stick composition as described in claim 4 which additionally contains from about 1% to about 10% of an emollient.
6. A solid stick composition as described in claim 5 wherein said emollient is selected from the group consisting of ethylene oxide condensation products, propylene oxide condensation products, fatty acid esters, fatty alcohol esters, water insoluble ethers, and mixtures thereof.
7. A solid stick composition as described in claim 6 wherein said astringent antiperspirant salt is a complex of aluminum chlorhydroxide, a zirconium compound and glycine.
8. An improved solid deodorant stick composition comprising
    a. from about 5% to about 20% of a long-chain fatty alcohol having from about 8 to about 18 carbon atoms in its chain;
    b. from about 35% to about 55% volatile silicone; and
    c. from about 0.1% to about 1.0% of a deodorant material
    wherein the improvement comprises improving the strength of said stick without undue brittleness by additionally including an alcohol selected from the group consisting of $C_{20}$ alcohol, alcohols whose claims are longer than $C_{20}$ and mixtures thereof, at a level of from about 1% to about 3% of the total fatty alcohol level.

* * * * *